US007724363B2

(12) United States Patent
Wachsmuth et al.

(10) Patent No.: US 7,724,363 B2
(45) Date of Patent: May 25, 2010

(54) DEVICE FOR MULTIFOCAL CONFOCAL MICROSCOPIC DETERMINATION OF SPATIAL DISTRIBUTION AND FOR MULTIFOCAL FLUCTUATION ANALYSIS OF FLUORESCENT MOLECULES AND STRUCTURES WITH FLEXIBLE SPECTRAL DETECTION

(75) Inventors: Malte Wachsmuth, Seoul (KR); Karsten Rippe, Heidelberg (DE); Gerrit Heuvelman, Wiesloch (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 921 days.

(21) Appl. No.: 11/324,892

(22) Filed: Jan. 4, 2006

(65) Prior Publication Data

US 2006/0146325 A1 Jul. 6, 2006

(30) Foreign Application Priority Data

Jan. 6, 2005 (DE) .................. 10 2005 000 915

(51) Int. Cl.
*G01N 21/64* (2006.01)
(52) U.S. Cl. .................. 356/317; 250/458.1
(58) Field of Classification Search ........... 356/317, 356/318, 417
See application file for complete search history.

(56) References Cited

U.S. PATENT DOCUMENTS

| 5,304,810 | A | * | 4/1994 | Amos ............... 250/458.1 |
| 5,886,784 | A | * | 3/1999 | Engelhardt ........... 356/326 |
| 6,262,423 | B1 | * | 7/2001 | Hell et al. ............ 250/458.1 |
| 6,555,811 | B1 | * | 4/2003 | Amos ................. 250/234 |
| 2004/0125372 | A1 | * | 7/2004 | Walla et al. ........... 356/318 |
| 2005/0213090 | A1 | * | 9/2005 | Namba et al. .......... 356/318 |
| 2006/0012872 | A1 | * | 1/2006 | Hayashi et al. ........ 359/386 |

FOREIGN PATENT DOCUMENTS

WO WO 2004/001402 A1 * 12/2003
WO WO 2004/036284 A1 * 4/2004

OTHER PUBLICATIONS

Brock, R. et al., "Rapid characterization of green fluorescent protein fusion proteins on the molecular and cellular level by fluorescent correlation microscopy," Proc. Natl. Acad. Sci. USA, vol. 96, Aug. 1999, pp. 10123-10128.
Koester, C. J., "Comparison of Various Optical Sectioning Methods," Handbook of Biological Confocal Microscopy, edited by James B. Pawley, Plenum Press, New York, 1995, pp. 525-534.
Lindek, S. et al., "Two New High-Resolution Confocal Fluorescence Microscopies (4Pi, Theta) with One- and Two-Photon Excitation," Handbook of Biological Confocal Microscopy, edited by James B. Pawley, Plenum Press, New York, 1995, pp. 417-430.
Description of the Leica TCS 4D Confocal Microscope, from Handbook of Biological Confocal Microscopy, edited by James B. Pawley, Plenum Press, New York, 1995, p. 588.

* cited by examiner

*Primary Examiner*—F. L Evans
(74) *Attorney, Agent, or Firm*—Houston Eliseeva LLP

(57) ABSTRACT

Many points on a sample are tested simultaneously in parallel in an FCS method with multifocal illumination and/or detection.

14 Claims, 3 Drawing Sheets

Plane from the x-axis and optical axis

Plane from the y-axis and optical axis

Plane from the x-axis and optical axis

Plane from the y-axis and optical axis

DEVICE FOR MULTIFOCAL CONFOCAL MICROSCOPIC DETERMINATION OF SPATIAL DISTRIBUTION AND FOR MULTIFOCAL FLUCTUATION ANALYSIS OF FLUORESCENT MOLECULES AND STRUCTURES WITH FLEXIBLE SPECTRAL DETECTION

RELATED APPLICATIONS

This application claims priority to German patent application number DE 10 2005 000 915.8 filed Jan. 6, 2005, which is incorporated herein by reference in its entirety.

BACKGROUND OF THE INVENTION

Systems known from the literature and from practice for combining fluorescence microscopy with FCS consist, for example, of a CLSM that is attached to an optical port of a microscope stand for the purpose of imaging, and of a separate illumination and detection unit for FCS that is attached to another port of the stand and serves to record and process the fluorescence signal at one point in each case (Zeiss). In a further implementation, fluorescence microscopy is effected via an epifluorescence setup and FCS measurement via a separate unit as just described (Brock, 1999). In a further implementation, imaging is effected using a CLSM, and the FCS excitation and detection unit via the same optic using the same (DKFZ) or separate detectors (Leica).

Intrinsic to all of the systems is that FCS measurement in particular may only be carried out at a single point on the sample at a time, and that the FCS measurement is carried out using conventional beam splitters and detection filters. The inherent, relatively long duration of an FCS measurement of at least a few seconds makes it very difficult to compare different measurement points with each other because living cells are analyzed in typical applications so that movements and structural changes occur within seconds and even faster and as a result well-defined positioning for different successive measurement points within the sample is difficult or impossible. The use, in particular, of the results of FCS analysis (as described above) as a contrast-providing signal for imaging in 1, 2, or 3 dimensions is thus made difficult or impossible. Furthermore, the detectors used for the FCS measurement must exhibit very high quantum yield and very good signal-to-noise ratio in order to be used for the photon counting needed for FCS measurements. Avalanche photo diodes (APDs) that possess a very small detector surface are primarily used, for which reason they are not suitable for spectral detection for which purpose they have been used to date (Leica, Zeiss).

A combination of fluorescence microscopy (e.g., confocal laser scanning microscopy; CLSM) and confocal fluorescence fluctuation spectroscopy (e.g., fluorescence correlation spectroscopy; FCS) permit the simultaneous imaging of the spatial distribution of fluorescent molecules in a sample and the dynamics of these molecules, e.g., as a result of movement processes such as directed transport or undirected diffusion. In existing systems and those known from the literature only one point at a time can be illuminated for fluorescence fluctuation analysis, and the associated fluorescence signal recorded and processed. In a raster-scan process, different points on the sample can be scanned successively.

SUMMARY OF THE INVENTION

The invention relates to a device for simultaneously illuminating several points on the sample (e.g., along a line) and for simultaneously recording and processing in parallel the fluorescent signal from these points. Processing comprises autocorrelation analysis of one and/or cross-correlation analysis of several spectral detection channels, analysis of the intensity distribution histogram in various channels, and similar methods, hereinafter referred to as FCS measurement. In particular, detection of the fluorescent signal can occur with the help of a spectrometer that enables flexible and freely selectable splitting of the fluorescence into several channels. Different groups of points on the sample may be scanned with the help of a beam scanner for moving the excitation points over the sample or with a sample scanner for moving the sample over the excitation points in order to record the spatial distribution of the fluorescence, and to determine the dynamic spatial resolution characteristics.

The object underlying the invention is to determine by imaging the spatial distribution of fluorescent molecules in a sample with spectrally resolved detection in one or several channels, and to record its dynamics simultaneously and in parallel with the help of FSC analysis of a multiplicity of points which may, for example, lie along a line, in one or several spectral channels.

Many sampling sites, and therefore, for example, the entire sample may be captured systematically in a raster-scan process with the help of a scanning device in which either the points of the illumination and detection unit are moved over the sample, or the sample is moved over the points of the illumination and detection unit. Parallelization enables the capture of many points simultaneously, and overall measurement of the various points is accelerated. In addition to pure fluorescence intensity, as is known for fluorescence microscopy, the results of FCS measurement, such as correlation times of dynamic processes (triplet kinetics, diffusion), particle counts molecular brightness, or reciprocal parameters of different molecules marked with fluorescence, may be used as contrast-providing signals for imaging. Furthermore, the fluorescent light should be captured by a freely and continuously adjustable spectral detection device and at the quantum yield required for FCS and the signal-to-noise ratio required for FCS, e.g., on detectors in the form of individual points or arrays of points, particularly along a line (line detector).

At comparably good spatial resolution of the multifocal CLSM, e.g., of a line scanner, imaging is considerably faster than with a point scanner.

FCS measurement at various points is also significantly accelerated by the simultaneous parallel capture of different points in comparison to systems with a single focus because FCS measurements may be conducted at different points simultaneously rather than sequentially. This enables the use of the results of an FCS measurement as contrast-providing imaging signals.

The combination of FCS and spectrally flexible detection, i.e., the ability to change the spectral detection region without changing filters or the like, enables more rapid adaptation to various experimental conditions.

The combination of FCS and CLSM in an optical system/apparatus enables very reproducible and calibration-free identification of FCS measurement points in a CLSM image.

The combination of FCS and spectrally flexible detection, i.e., the ability to change the spectral detection region without changing filters or the like, permits spectral redundancy, i.e., there are more detection channels than types of fluorophors, which in turn may improve the signal-to-noise ratio.

Simultaneous measurement of the fluorescent signal at various points enables measurement, by means of temporal-spatial correlation analysis of the signals, of the characteristics of directed transport processes such as direction and velocity, particularly when the measurement points are arrayed along a straight line.

Simultaneous FCS measurement at different points in non-structured samples, such as fluorescent molecules in solution, permits a significantly faster determination of characteristics such as partial concentrations, diffusion coefficients, and the interaction between different types of molecules, because instead of a long FCS measurement at a single point, many short simultaneous FCS measurements lead to the same results with the same level of statistical quality.

Particularly advantageous implementations comprise, for example:
  FCS with multifocal illumination/detection, i.e., preferably at many points simultaneously in parallel, and/or
  FCS with detection in a spectrometer and one or several spectrally flexible continuously adjustable detection channels, and/or
  CLSM with multifocal illumination/detection combined with detection in a single spectrometer and one or several spectrally flexible, i.e., programmable, detection channels, and/or
  Multifocal may, in particular, mean: many points simultaneously along a line (line scanning system), and/or
  The combination of a multifocal apparatus, in particular a line scanner, and laterally structured illumination and/or axial resolution improvement, conditional on interferometry (e.g., 4-pi apparatus).

The object of the invention is schematically represented by the figures and is described below based on the figures, wherein components that function identically are given the same reference numbers.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
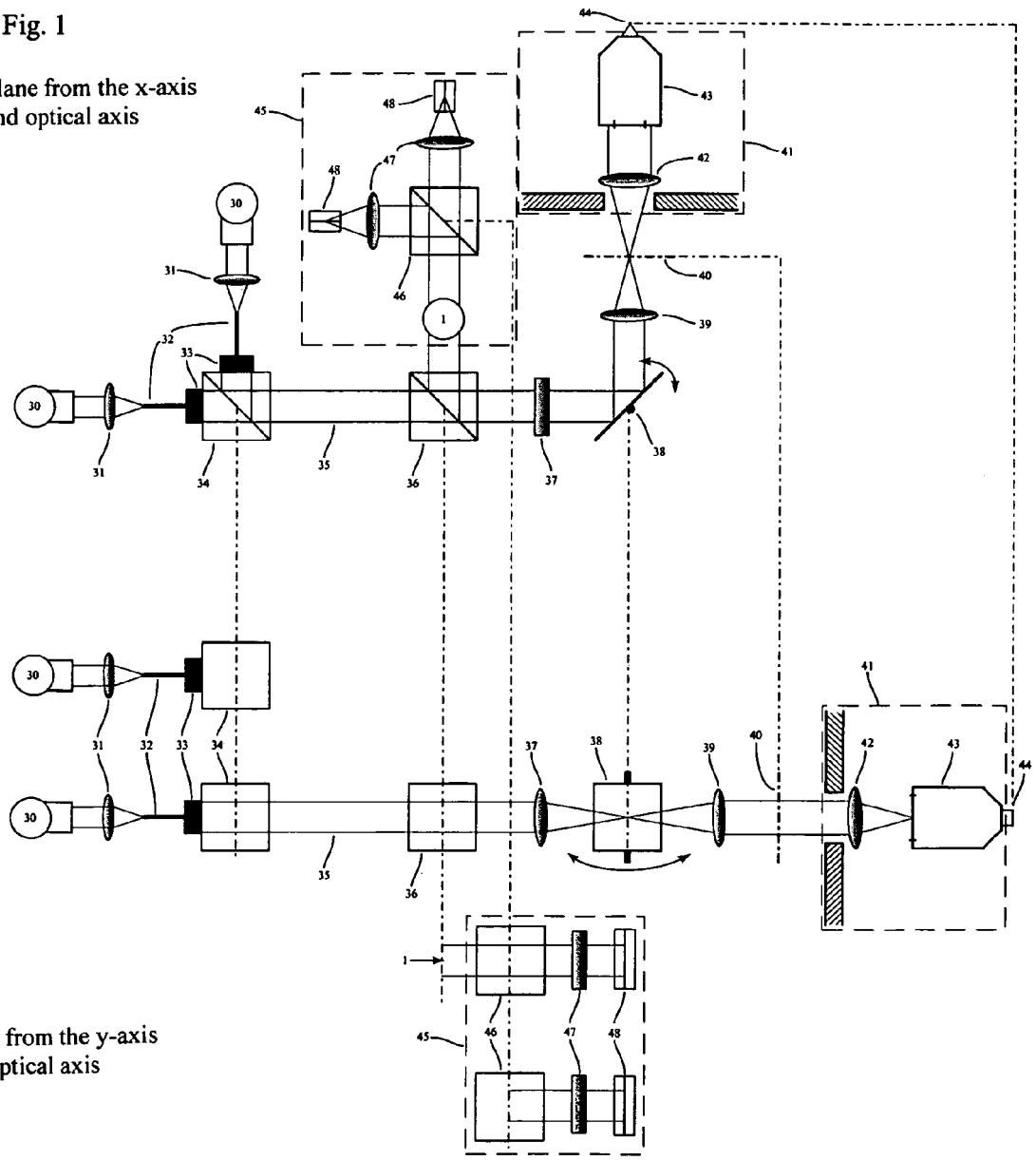
FIG. 1 is an illustration of a plane from the x-axis and optical axis.

FIG. 1 shows a possible implementation of a line scanner as described, for example, in Pawley (1995) as a translation of the multifocal concept. Light from one or several lasers 30 are coupled in a fiber 32 via an optic 31 and collimated with the help of an output/collimation optic 33 and directed toward a beam combiner 34. Combination of several lasers may also result from cascading. The collimated light 35 can be spread asymmetrically in x-direction and y-direction by an anamorphotic expander because it is focused on a point in x-direction and on a line in y-direction. The laser light is directed through a beam splitter 36 and a cylindrical lens 37 that is implemented such that it has no effect in x-direction, and in y-direction focuses the light onto the center of a rotatable mirror 38 that is perpendicular to the midline. This mirror may be rotated in a well-defined manner, e.g., with a galvanometric drive. At the same time, the center of the mirror is located in the focal plane of a spherical scanning lens 39, preferably a so-called F-Theta lens, that with the help of the mirror transforms the rotation of the light bundle into a lateral movement in x-direction in the intermediate image plane 40 of the microscope 41. Simultaneously, the light is focused on a point in x-direction and on a line in y-direction in the intermediate image plane 40. This line is imaged with the help of the tube lens 42 and the objective 43 in the focal plane 44 of the object side. The fluorescent light excited by the laser light is then recollected via the same optic, separated from the excitation light with the help of the beam splitter 36, and directed to the spectral detection unit 45. There, it is directed to one or several line detectors 48 with the help of one or several dispersion elements 46 and with filters with fixed or freely selectable spectral characteristics, as well as with the help of suitable optics, e.g. cylindrical optics 47. Slit apertures may be located in a focal conjugated image plane 40 between the detectors 48 and the beam splitter 36, which ensures confocality. In particular, an anamorphotic beam waist adapter may be introduced before or after the dispersion element 46. As a result, the line in the object plane 44 is first imaged via the microscope in the intermediate image plane 40 and then on the line detector 48. To capture the image, the line is moved systematically through the sample by rotating the scanner mirror 38, and the corresponding signal is recorded synchronously by the detectors 48 so that the spatial distribution of fluorescent molecules/structures may be reconstituted in a computer. Because the points of an entire line art captured simultaneously instead of serially, a significantly higher image rate may be achieved than with a point scanner. For FCS measurement, a line may be selected in a previously captured image that is then illuminated for a selectable time by means of a correspondingly fixed rotational positioning of the scanning mirror 38. The fluorescent light from points along this illuminated line is simultaneously recorded in parallel and processed according to an FCS measurement. A line detector may include individual lines of CCD or CMOS array chips, CCD or CMOS line ships, or linear arrays of photo diodes or photomultipliers. Avalanche photo diodes (APDs) and CCD or CMOS arrays are particularly well-suited because of their especially high quantum yield and their good signal-to-noise ratio.

In a possible embodiment, structured illumination is imposed in y-direction that is imaged in the sample and improves the resolution in the presence of collimated light 35 with the help of suitable elements such as interference superimposition, laser beams slightly tipped in y-direction, a neutral filter with periodic transmission in y-direction, or a periodic transmission grid in y-direction.

In a further embodiment, the light, as is known from point confocal 4-pi microscopy (Pawley, 1995) and standing wave epifluorescence microscopy, is split between two objectives that are positioned opposite each other so that additional improvement in resolution along the optical axis is achieved by interference.

Figure 2:
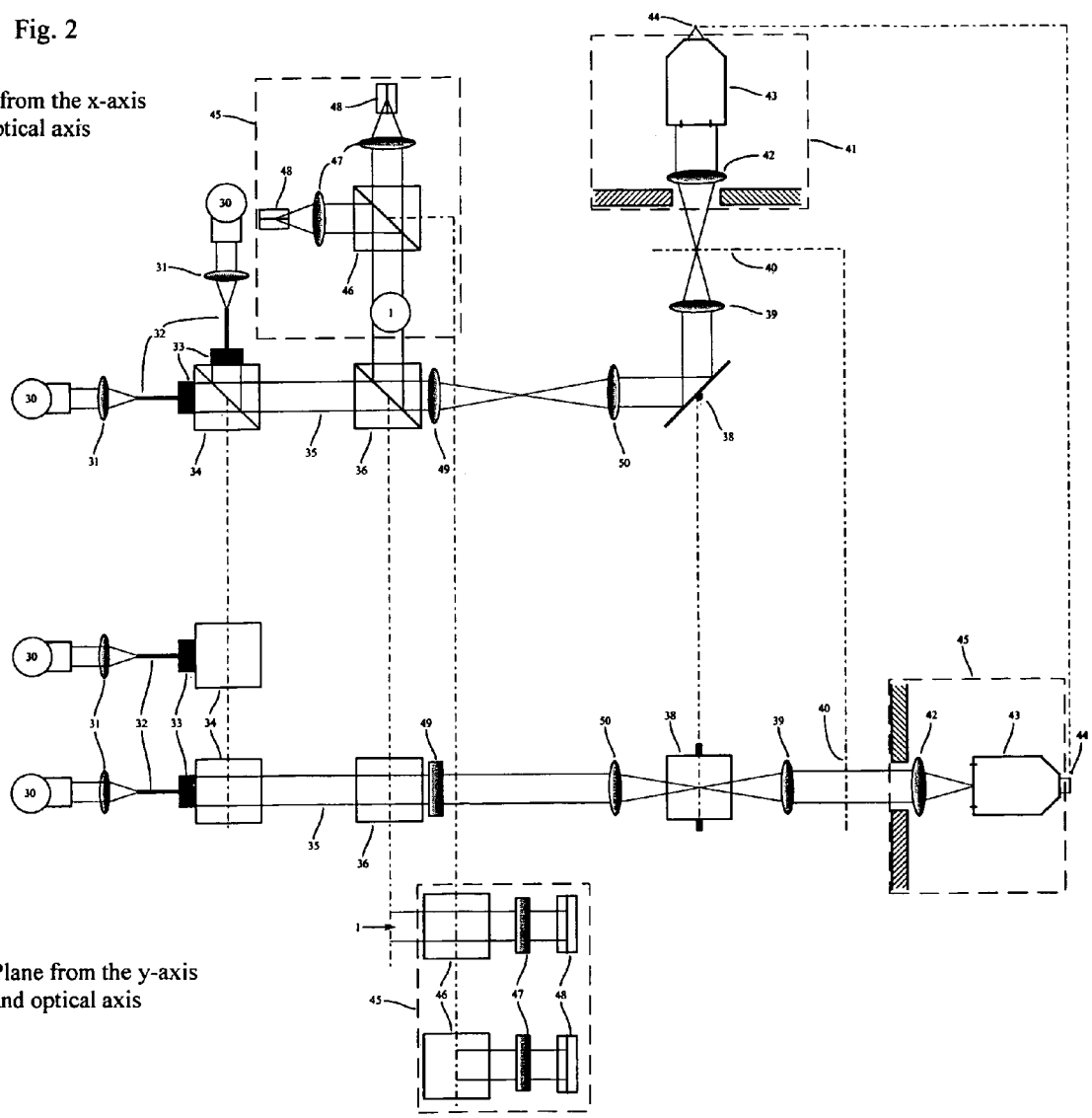
FIG. 2 is an illustration of a plane from the 7-axis and optical axis

FIG. 2 shows an embodiment of the apparatus shown in FIG. 1, in which a cylindrical lens 49 focuses the light in x-direction onto a point and leaves it unchanged in y-direction. This point lies on the focal plane of a spherical lens 50, ideally with the same characteristics as the scanning lens 39, in which other focal plane the rotatable galvanometric mirror 38 is located, and which recollimates the beams in x-direction and focuses them in y-direction on the rotational axis of the galvanometric mirror 38.

The beam paths for a line scanner for imaging and FCS measurement that are represented are examples and may also be realized in modified form.

Figure 3:
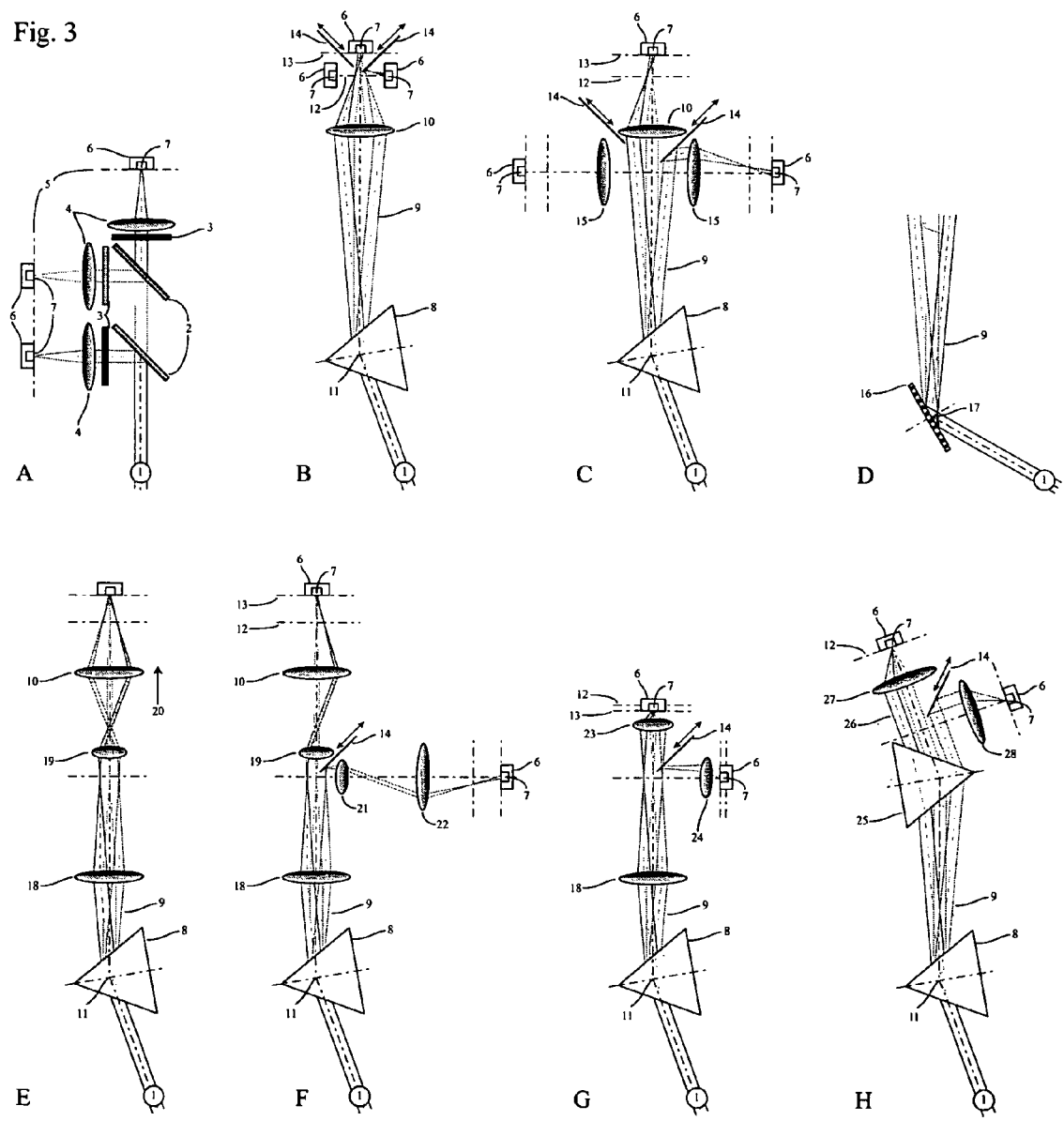
FIG. 3 is an illustration of possible implementation of spectral detection units.

FIG. 3 shows a possible implementation of spectral detection units 45 with fixed or selectable spectral regions of the detection channels, which are suitable for both point detectors with a spherical optic and for line detectors with a cylindrical optic.

Implementation A is state-of-the-art (Pawley, 1995) with dichroic mirrors 2 and filters 3 selected such that with the help of lenses 4, the desired segments of the spectrum of incident collimated light 1 strike the detectors 6 with their light-sensitive regions 7. The light of insensitive region 7 may be punctiform or a line of point detectors, i.e., a line detector. The number of channels (3) represented is only an example. Implementations B, C, D, E, F, G, and H are new in the sense of the invention because for a single freely selected spectral region they permit detection with a detector suitable for FCS measurement that, in comparison to a photomultiplier, comprises a significantly smaller detection surface.

In Implementation B, the collimated light I is spectrally split into a parallel beam bundle 9 with the help of a dispersion element such as a prism 8. In the process, the angle of deflection caused by the dispersion element is dependent on the wavelength of the light. A lens 10 is implemented such that its focal length is significantly smaller than its distance from the apparent pivot 11 of the light bundle. It then focuses the light in the focal plane 12 in convergent beams that are tilted toward the optical axis. A focused image of the spectrum is located there. The divergent beams behind the focal plane run together in a plane 13 in which they strike a detector 6. The spectral regions that strike the detector that lies on the optical axis and on the detectors 6 that are rotated out of the axis may be selected with the help of sliding absorbent and/or reflective apertures 14 that are preferably located in the focal plane 12 and may also be implemented as a combined pair in an absorbent and a reflective version. A sufficiently small beam diameter/beam breadth strikes the detector when the distance between the lens 10 and the pivot 11 are significantly greater than the focal distance of the lens 10 and in addition, the beam diameter/beam breadth of the parallel beam bundle 9 is as small as possible. Good spectral resolution is obtained when the beam divergence of the parallel beam bundle 9 is as large as possible.

Implementation C corresponds to B. However, the apertures/mirror sliders 14 are here located in front of the lens 10. The desired spectral regions, which lie either on the detection beam path that lies on the optical axis (consisting of the lens 10 and detector 6) or on the conjugated detection beam paths 15, 6 that are rotated out of the optical axis to 10, 6, are selected from the collimated beams 9 by sliding. In this implementation as well, a large possible divergence and/or a small as possible beam diameter/beam breadth of the collimated beam bundles of 9 are desirable.

Implementation D shows that the dispersion element may be a prism 11, a grid 16, or any other element that splits incident collimated light into a bundle of spectrally split collimated beams, whereby the angle of deflection is dependent on the wavelength.

Implementation E shows a device with a telescope (implemented, for example, with lenses 18 and 19 in a Keplerian arrangement, although it may be implemented differently) beam diameter/beam breadth of 9 reduced by a factor, and the divergence of the collimated bundle of 9 enlarged by the same factor, so that in 20 in comparison to 9 the desired requirements of B and C are better met. Here, the focal point of the lens 18 lies in the apparent pivot 11.

Implementation F utilizes the fact that a real intermediate image plane exists in the Keplerian telescope. The divergent bundle of collimated beams is imaged there as a sharp spectrum so that spectral regions in the sliding apertures 14 may be selected in the intermediate image plane and strike the detectors that lie on the optical axis 19, 10, 7, or that are directed from the detection beam paths 21, 22, 7 that are tipped away from it, as represented in E.

In implementation G, the spectrum that is produced and focused via the lens 18 is selectively split between various beam paths 23, 7 and 24, 7 by means of sliding apertures 14. Lenses 23 and 24 are arranged such that they produce an inverted image 6f the spectrum in 12. Because the focal point of 18 lies in 11, the inversion effects a convergence of all convergent beams in plane 13 in front of the focal plane. The detector is positioned there. The distance between the lenses 23 and 24 is significantly smaller than the distance of the focused spectrum between lens 18 and lenses 23 and 24 so that the beam diameter/beam breadth in 13 is as small as possible.

Implementation H is characterized in that the divergent bundles of collimated beams 9 are directed through a further prism 25 that is rotated by 180° so that a parallel bundle of collimated beams 26 is produced. The position perpendicular to the direction of the beam depends on wavelength. Spectral regions may be selected by means of sliding apertures 14 from this parallel bundle of collimated beams and may be focused on various detectors 6 by means of lenses 27 and 28. Here, the distance between the prisms should be as large as possible and the beam diameter/beam breadth 9 as small as possible in order to obtain good spectral resolution.

While this invention has been particularly shown and described with references to preferred embodiments thereof, it will be understood by those skilled in the art that various changes in form and details may be made therein without departing from the scope of the invention encompassed by the appended claims.

What is claimed is:

1. A device for fluorescent correlation spectroscopy comprising
    a confocal scanning microscope and
    a line scanning system using at least two collimated illumination beams,
    wherein many points on a sample are tested simultaneously in parallel using multifocal illumination and/or detection.

2. The device according to claim 1, wherein the line scanning system has a multifocal construction and a laterally structured illumination and/or interferometrically conditioned axial resolution improvement.

3. A device for fluorescent correlation spectroscopy comprising
    a confocal scanning microscope and
    a spectrometer,
    wherein many points on a sample are tested simultaneously in parallel using multifocal illumination and/or detection.

4. A device for fluorescent correlation spectroscopy comprising
    a confocal scanning microscope and
    one or several spectrally flexible continuously adjustable detection channels,
    wherein many points on a sample are tested simultaneously in parallel using multifocal illumination and/or detection.

5. A confocal microscope comprising:
- multifocal illumination and/or detection with detection in a spectrometer and
- a line scanning system using at least two collimated illumination beams,
- one or several spectrally flexible or programmable detection channels.

6. The confocal microscope according to claim 5, wherein many points on a sample may be tested simultaneously in parallel.

7. The confocal microscope according to claim 6, further comprising a spectrometer.

8. The confocal microscope according to claim 5, further comprising one or several spectrally flexible continuously adjustable detection channels.

9. The confocal microscope according to claim 5, wherein the line scanning system has a multifocal construction and a laterally structured illumination and/or interferometrically conditioned axial resolution improvement.

10. A method of fluorescent correlation spectroscopy comprising:
- testing multiple points on a sample simultaneously in parallel by line scanning with at least two collimated illumination beams,
- using a confocal scanning microscope, and
- providing multifocal illumination and/or detection.

11. The method according to claim 10, wherein the points to be tested simultaneously in parallel lie on a line.

12. The method according to claim 10, further comprising using a line scanner having a multifocal construction and a laterally structured illumination and/or interferometrically conditioned axial resolution improvement.

13. A method of fluorescent correlation spectroscopy comprising:
- testing multiple points on a sample simultaneously in parallel,
- using a confocal scanning microscope,
- providing multifocal illumination and/or detection, and
- detection by a spectrometer.

14. A method of fluorescent correlation spectroscopy comprising:
- testing multiple points on a sample simultaneously in parallel,
- using a confocal scanning microscope,
- providing multifocal illumination and/or detection, and
- using one or several spectrally flexible continuously adjustable detection channels.

* * * * *